United States Patent
Charrin et al.

(12) 
(10) Patent No.: US 6,245,926 B1
(45) Date of Patent: Jun. 12, 2001

(54) PREPARATION OF ALKYLMONOHYDROGENOHALOGENOSILANES BY REDISTRIBUTION FOLLOWED BY DISTILLATION AND ASSOCIATED DEVICE

(75) Inventors: Jean-Jacques Charrin, Lyons; Pascale Colin, Chassieu; Raphael Guinamard, La Mulatiere; Françoise Igersheim, Lyons; Gilbert Margeriat, Ville Sous Anjou, all of (FR)

(73) Assignee: Rhodia Chimie, Boulogne Billancourt (FR)

( * ) Notice: Subject to any disclaimer, the term of this patent is extended or adjusted under 35 U.S.C. 154(b) by 0 days.

(21) Appl. No.: 09/581,353

(22) PCT Filed: Dec. 9, 1998

(86) PCT No.: PCT/FR98/02672

§ 371 Date: Aug. 11, 2000

§ 102(e) Date: Aug. 11, 2000

(87) PCT Pub. No.: WO99/31111

PCT Pub. Date: Jun. 24, 1999

(30) Foreign Application Priority Data

Dec. 12, 1997 (FR) .................................................. 97 16047

(51) Int. Cl.⁷ ....................................................... C07F 7/08
(52) U.S. Cl. .............................................................. 556/469
(58) Field of Search ............................................. 556/469

(56) References Cited

U.S. PATENT DOCUMENTS 4,349,417  9/1982  Rebsdat ................................. 203/33
4,645,570  2/1987  Sridhar .................................. 203/73
5,493,043 * 2/1996  Marko .................................. 556/469
5,654,459 * 8/1997  Kropfgans et al. .................. 556/469
6,077,967 * 6/2000  Cardinaud et al. .................. 556/469

FOREIGN PATENT DOCUMENTS 2119477    8/1972  (FR) .

* cited by examiner

Primary Examiner—Paul F. Shaver
(74) Attorney, Agent, or Firm—Jean-Louis Seugnet

(57) ABSTRACT

The invention concerns a method for obtaining alkylmonohydrogenohalogenosilanes (AHHS), for example $Me_2HSiCl$. Said AHHS are prepared by redistribution from $MeHSiCl_2$ and $Me_3HSiCl$ in the presence of a catalyst such as $AlCl_3$, which can start a parasitic disproportionation which affects the AHHS produced. In order to avoid this, the method consists in using an inhibitor which neutralizes $AlCl_3$ after redistribution, The problem which still prevails and on which the present invention is based is related to the fact that during distillation, which aims at separating the required AHHS, the latter are again subjected to the parasitic disproportionation. In order to solve this problem, the invention proposes a method for preparing AHHS comprising steps (a) of redistribution, (b) use of an inhibitor of $AlCl_3$ and (c) separating and collecting by distillation AHHS formed in the raw reaction mixture of redistribution using three distillation columns I, II, III and proceeding in such a way that, at least in one part of the distillation circuit, the AHHS aimed at are in the presence of the $AlCl_3$ inhibitor. Advantageously, the inhibitor is injected in the reflux of column I top. The invention also concerns a train of three distillation columns comprising means of injecting the $AlCl_3$ inhibitor.

11 Claims, 1 Drawing Sheet

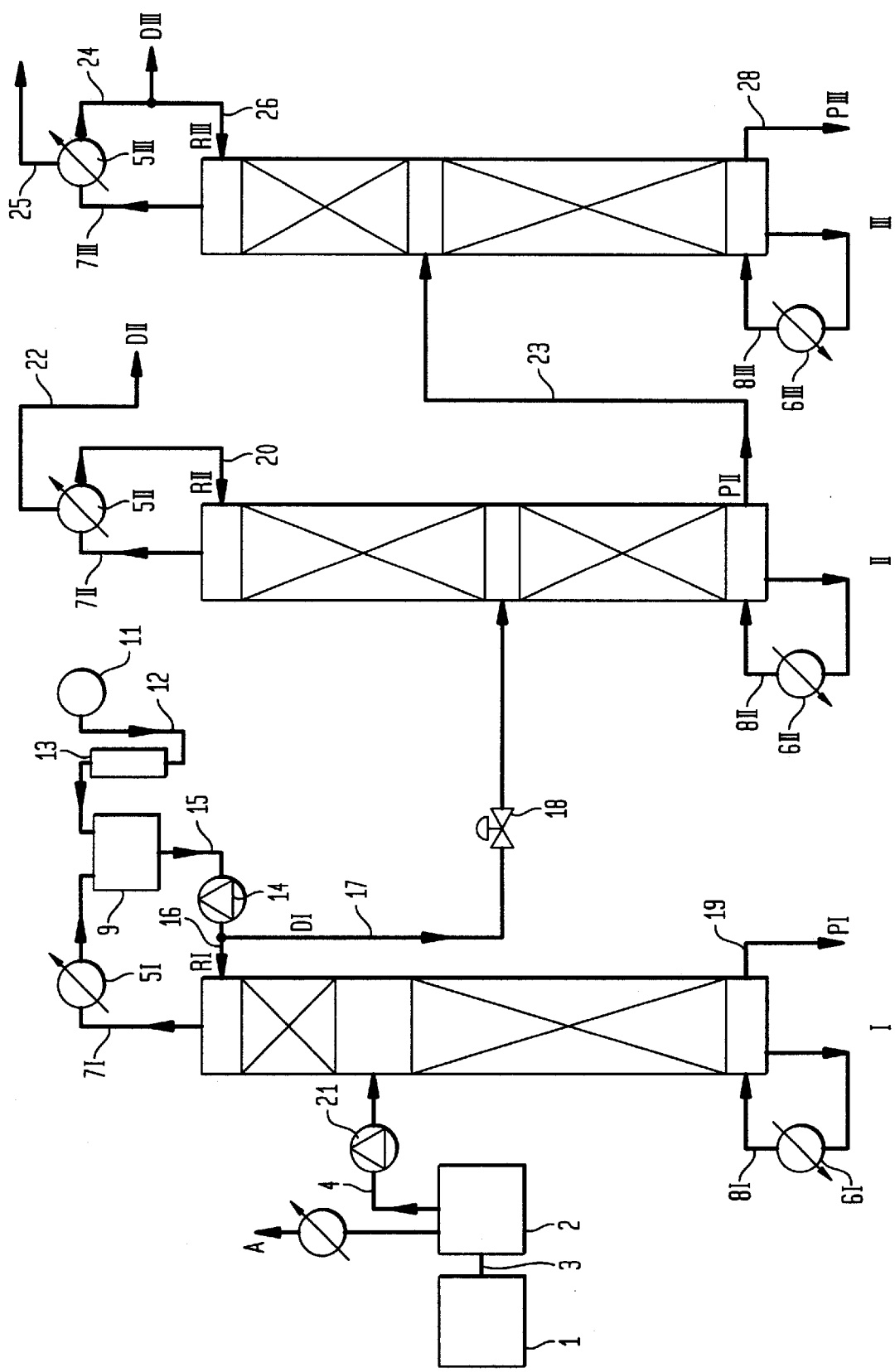

PREPARATION OF ALKYLMONOHYDROGENOHALOGENOSILANES BY REDISTRIBUTION FOLLOWED BY DISTILLATION AND ASSOCIATED DEVICE

This application is an application under 35 U.S.C. Section 371 of International Application Number PCT/FR98/02672 filed on Dec. 9, 1998.

The present invention relates to the production of alkylmonohydrosilanes, which are starting materials particularly prized in organosilicon chemistry. More specifically, the invention relates to the separation of these alkylmonohydrohalosilanes (AHHSs) within complex mixtures obtained on conclusion of double exchange (or redistribution) reactions of alkyl and halogen substituents between halogenated silanes which may or may not result from direct synthesis, at least one of these silanes being a hydrosilane. This separation is carried out by distillation and the present invention is more specifically an improvement to this stage.

Without this being limiting, the present invention is targeted very specially at purifying a dialkylhydrochlorosilane produced by redistribution from a chlorinated alkylhydrosilane and an optionally chlorinated alkylsilane. This mono- or dialkylhydrochlorosilane is a synthetic agent which is particularly valued in very numerous and varied applications, for example in the preparation of organosilicon monomers or of more condensed base compounds.

The starting materials for this redistribution are obtained by direct synthesis. This technique consists in reacting alkyl chloride with silicon in the presence of a copper catalyst in order to form alkylchlorosilanes. The main product from this synthesis is dialkyldichlorosilane. The other coproducts are: monoalkylhydrodichlorosilane, dialkylhydrochlorosilane, trialkylchlorosilane and alkyltrichlorosilane.

It would have been possible to imagine isolating mono- and dialkylhydrochlorosilanes by distillation from the reaction mixture produced by direct synthesis. However, in so far as this mono- and this dialkylhydrochlorosilane are minor coproducts of the direct synthesis, it is clear that this route for obtaining them is not advantageous.

It follows that to produce mono- and dialkylchlorosilanes (e.g. $Me_2HSiCl$), it is preferable, in accordance with the present invention, to recover these products from the crude mixture originating from the redistribution between an alkylhydrodichlorosilane and a trialkylchlorosilane or between an alkylhydrodichlorosilane and a tetraalkylsilane.

The redistribution between the alkyl, chlorine and hydrogen substituents of the silicons is carried out in the presence of catalysts, such as Lewis acids.

Throughout the present account, Me denotes the monovalent radical $CH_3$.

French Patent FR-A-2,119,477 gives a good illustration of this technique for the preparation of dialkylhydrochlorosilanes by redistribution. The process disclosed in this document consists in reacting methylhydrodichlorosilane and trimethylchlorosilane in an $MeHSiCl_2/Me_3SiCl$ molar ratio of the order of 0.5 in the presence of a catalyst formed by $AlCl_3$.

The reaction mixture is placed in a reactor under an autogenous pressure of 3 to $5 \times 10^5$ Pa. The reaction takes place for several hours at a temperature of between 85 and 170° C. This redistribution results in $Me_2HSiCl$ and in numerous byproducts. On completion of the distillation, it is apparent that the yield for separation of $Me_2HSiCl$ is abnormally low, since it peaks at approximately 71%. Such results must be regarded as unsatisfactory with regard to industrial profitability.

To improve this state of the art, provision has been made by the Applicant in French Patent Application No. 9607569 of Jun. 12, 1996, which has not yet been published, to employ inhibition of the redistribution catalyst as soon as it has fulfilled its role in the reaction under consideration. This provision makes it possible to decrease, indeed even to eliminate, an interfering phenomenon induced by the $AlCl_3$ catalyst during the distillation, namely the dismutation of the chlorinated dialkyl(methyl)hydrosilane which it is desired to purify. It is clear that such a dismutation phenomenon is entirely harmful to the yield of $Me_2HSiCl$.

The inhibitors provided in this improvement are polyorganosiloxanes or (poly)silanes which are provided in the fluid form or in the resin form and which are optionally alkoxylated. The metal of the catalyst/oxygen of the inhibitor molar ratio is chosen within a range of values which are less than 0.9.

These improvements have made it possible to significantly increase the yields of dialkylhydrochlorosilane. Thus, after redistribution, a distillate is obtained composed of a mixture of redistribution products rich in dialkylhydrohalosilane (e.g. $Me_2HSiCl$), since the interfering dismutation has been eradicated.

However, when attempts are made to isolate the alkylhydrohalosilane(s) from the crude redistribution mixture by distillation, a substantial loss in AHHS (e.g. $Me_2HSiCl$) is observed.

Confronted with this technical problem of loss of mono- or dialkylhydrochlorosilanes during distillation, the Applicant Company has set itself the essential objective of solving it.

Another essential objective of the present invention is to provide a process for the preparation of alkylmonohydrohalosilanes (e.g. $Me_2HSiCl$ or $MeHSiCl_2$) which resolves the problem targeted above and which is particularly simple to employ and economical.

Another essential objective of the invention is to provide a process for the preparation of alkylmonohydrohalosilanes (e.g. $Me_2HSiCl$ or $MeHSiCl_2$) which resolves the problem targeted above, which is as defined above and which makes it possible in particular to obtain these products with high levels of purity.

In order to be able to achieve these objectives, inter alia, the Applicant Company has had the credit of demonstrating a problem specific to the use of the process for the preparation of alkylmonohydrochlorosilanes and more particularly still to the distillation phase characteristic of this process. This is because the Applicant Company has been able to show that the distillation columns can be the site of undesirable dismutation reactions of alkylmonohydrochlorosilanes because of the presence of traces of aluminium-comprising products which can be aluminium chloride and/or organoaluminium compounds and/or silicon/aluminium compounds and/or organosilicon/aluminium compounds. These traces of aluminium-comprising products (e.g. $AlCl_3$) promote the conversion of the redistribution products to byproducts of the optionally chlorinated organosilane and organohydrosilane type. Thus it is that, for example, $Me_2HSiCl$ is converted to $Me_2SiH_2$ and to $Me_2SiCl_2$ because of this interfering dismutation. It is clear that the latter seriously interferes with this separation phase of the process for the preparation of organohydrohalosilanes (AHHSs).

In addition to updating the technical problem, the inventive step of the Applicant Company has been complemented and enriched by the development of provisions which consist in choosing the appropriate temperature variables and in deactivating the compounds present in the distillation circuit with the AHHSs which are capable of acting as dismutation catalysts for the latter. It follows that the present invention relates to an industrial and continuous process for the preparation of alkylmonohydrohalosilanes (AHHSs) which are liable to be subject to a dismutation catalysed by at least one Lewis acid, this process being of the type of those comprising the following essential stages:

(a) redistribution between at least one first compound of formula (1): $(R)_a(H)_bSiX_{4-a-b}$, and at least one second compound of formula (2): $(R')_cSiX_{4-c}$, (1) and (2) being formulae in which:
* a=0, 1, 2 or 3; b =1, 2 or 3; c 1, 2, 3 or 4 and a+b <3;
* R and R' are radicals which are identical to and/or different from one another and which are chosen from alkyls and/or aryls (preferably methyl, ethyl, propyl or phenyl);
* the X substituents are identical to or different from one another and correspond to a halogen, preferably Cl, with the condition according to which at least one X atom is present in at least one of the two compounds of formulae (1) and (2), the said redistribution taking place in the presence of a catalyst chosen from Lewis acids, preferably from metal halides and/or borates and more preferably still from the group consisting of: $AlCl_3$, $ZrCl_4$, $KAlCl_4$, $CuCl$, $H_3BO_3$ and $BF_3$;

(b) introduction into the reaction mixture of at least one inhibitor of the redistribution catalyst;

(c) separation and collection, preferably by distillation, of the alkylmonohydrosilanes formed in the crude redistribution reaction mixture (a);

characterized

▲ in that, in the context of the stage (c), the crude reaction mixture is subjected to a distillation treatment involving at least one distillation column, ▲ and in that it is seen to that, at least in a portion of the distillation circuit, the targeted AHHSs are in the presence of at least one inhibitor of any product capable of behaving as a redistribution catalyst with respect to the said AHHSs.

Concern for the continual inhibition of the compounds which catalyse dismutation in the distillation circuit makes it possible to obtain, at the end of distillation, the targeted AHHSs in an extremely pure form.

The distillation at the heart of the process according to the invention can be carried out according to a batchwise or continuous mode using one or more distillation columns (line of columns). The use of a line of columns is favoured industrially.

The line of distillation columns which is employed in a stage ($c_1$) of the process according to the invention comprises at least two columns (I, II, . . . N), preferably at least three columns.

In order to ensure the presence of inhibitors throughout the distillation circuit, at least one injection or incorporation of inhibitors in the circuit is carried out in accordance with the invention. This operation, which will be referenced as ($c_2$) in the present account, is advantageously carried out as indicated hereinbelow:

(i) → by injecting a fluid (preferably a liquid) comprising the inhibitor,

Δ on the one hand, at least into the first column (I) of the distillation line, countercurrentwise with respect to the fluid vapour comprising the AHHSs, Δ and, on the other hand, into the feed fluid for the second column (II);

(ii) → and/or by mixing the inhibitor with the feed fluid for at least one of the columns (II to N) of the line, preferably for the column (II).

In accordance with the invention, the alternative form (i) is very particularly used in practice.

According to a preferred provision of the invention, the stage ($c_2$) is carried out by mixing the fluid comprising the targeted AHHSs with the condensate ($D_I$) produced and collected at the top of column (I) and by providing for the reflux $R_I$ of at least a portion of this condensate into this column (I);

the reflux ratio $r_I = R_I/D_I$, with $R_I$=reflux at the top of column (I) and $D_I$=distillate at the top of column (I), preferably being adjusted to between 0.5 and 3, preferably between 1.5 and 2.5 and more preferably still to a value of the order of 2.

The column I is intended for the tailing of the fluid to be distilled, that is to say for the removal of the redistribution catalyst (e.g. $AlCl_3$) and of its inhibitor (e.g. decamethylpentasiloxane).

The column II is intended for the separation by topping of the lightest compounds of the crude reaction mixture, that is to say, for example, alkyldihydrohalo(chloro)silanes $MeH_2SiCl$ and $Me_2H_2Si$.

The column III is intended for the final isolation by tailing of the targeted alkylmonohydrosilanes (e.g. $Me_2HSiCl$). The residue from this column III comprises alkylchlorosilanes (e.g. $Me_3SiCl$ and $Me_2SiCl_2$).

The AHHSs which it is desired to purify, the complex mixture from which they originate and the equipment used will be the determining factors in establishing the distillation procedure (number of theoretical stages, reflux ratio, temperatures and pressures at the column bottom and top, feed point).

According to preferred forms of the process according to the invention, the column (I) is fed with the crude reaction mixture while having taken care to set the pressure parameters ($P_{bI}$, $P_{tI}$) and temperature parameters ($\theta_{bI}$, $\theta_{tI}$) for the bottom and top of the column, number n, of plates and reflux ratio r, so that a distillation fraction comprising the targeted AHHS is recovered at the top of column (I).

This fraction is subsequently condensed into a liquid which is fractionated into a reflux $R_I$ and into a distillate $D_I$.

The inhibitor is incorporated according to the alternative form (i) defined hereinabove, before or after, preferably before, the bypass separating, on the one hand, DI and, on the other hand, $R_I$.

It follows that a portion of the inhibitor flows back into the column (II) via $R_I$ and it is particularly surprising to find that this inhibitor portion, a very minor amount, which flows back, is nevertheless sufficient to extinguish the interfering dismutation.

The reflux ratio $r_I$ of the top condensate of the first column (I) is such that the reflux $R_I$ represents from 60 to 80% by volume, preferably 70 to 75% by volume, of the total amount of condensate produced, against 40 to 20% by volume, preferably 30 to 25%, for the fraction DI drawn off and conveyed to the following column (II).

The feeding of the column (II) with $D_I$ is accompanied with the choice of the distillation parameters, namely: pressures ($P_{bII}$, $P_{tII}$) and temperatures ($\theta_{bII}$, $\theta_{tII}$) for the bottom and top of the column, number $n_{II}$ of plates and reflux ratio $r_{II}$, so as to produce and collect:

➤ on the one hand, at the top of column (II), a distillation fraction forming the distillate ($D_{II}$) and comprising alkylhydrohalosilanes and alkylsilanes with boiling points which are below that of the targeted AHHS, ➤ and, on the other hand, at the bottom of column (II), a distillation fraction $P_{II}$ comprising the targeted AHHS.

Advantageously, in practice, virtually all the gaseous fluid produced at the top of column (II), with the exception of the light fractions (e.g. MeH$_2$SiCl, Me$_2$H$_2$Si), is condensed. The gas with the light fractions is discharged from the distillation circuit in order to be enhanced in value or incinerated. The liquid condensate forming the remainder of $D_{II}$ partially or completely, preferably completely, flows back into the top of column (II).

In accordance with the invention, the bottoms $P_{II}$ are drawn off and conveyed to the feed point for the column (III). Care was taken, furthermore, to set the pressure parameters ($P_{bIII}$, $P_{tIII}$) and temperature parameters ($\theta_{bIII}$, $\theta_{tIII}$) for the bottom and top of the column, number $n_{III}$ of plates and reflux ratio $r_{III}$ so as to produce and collect:

⇨ on the one hand, at the top of the column, a distillate $D_{III}$ composed essentially of the targeted AHHS, ⇨ on the other hand, at the bottom of the column, a distillation fraction forming the bottoms PI,, comprising alkylhydrohalosilanes and alkylhalosilanes with boiling points which are greater than or equal to that of the targeted AHHS.

In practice, the distillate $D_{III}$ is preferably condensed and the possible impurities still present (e.g. Me$_2$H$_2$) can, if appropriate, be discharged in the gaseous form.

In addition to the distillation parameters, the choice of the inhibitor is also a significant component of the invention. Thus, the preferred inhibitors are:

cyclic polyorganosiloxanes (POS) comprising from 4 to 10 Si atoms, octamethyltetrasiloxane (D$_4$) and decamethylpentasiloxane (D$_5$) being preferred;

a hydroxylated or non-hydroxylated, linear or branched POSs having from 2 to 100 silicon atoms and more preferably still polydimethylsiloxanes with a viscosity of 50 mPa.s;

optionally alkoxylated POS resins;

optionally alkoxylated silanes;

monofunctional or polyfunctional alcohols (e.g. ethanol);

ketones (e.g. acetone);

and their mixtures.

More specifically, when it is a silicone compound, the inhibitor can be:

(i) a linear or substantially linear POS composed of units of formula (4), terminated at one of the ends of the chains by a unit of formula (5) and at the other end by a unit of formula (6), (2i) a cyclic POS composed of units of formula (4), (3i) a mixture of several components (i) or (2i) with one another, (4i) a mixture of one or more component(s) (i) with one or more component(s) (2i),

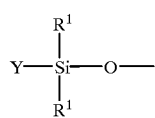

(5)

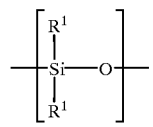

(4)

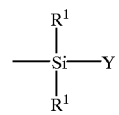

(6)

in which formulae:

the $R^1$ symbols are alike or different and each represent a linear or branched $C_1$–$C_8$ alkyl radical optionally substituted by one or more halogen(s), such as, for example, methyl, ethyl, propyl, octyl or 3,3,3-trifluoropropyl; a $C_5$–$C_8$ cycloalkyl radical, such as, for example, cyclohexyl or cycloheptyl; or a $C_6$–$C_{12}$ aryl radical or an aralkyl radical having a $C_6$–$C_{12}$ aryl part and a $C_1$–$C_4$ alkyl part, which radical is optionally substituted on the aromatic part by one or more halogen(s), $C_1$–$C_3$ alkyl (s) and/or $C_1$–$C_3$ alkoxy(s), such as, for example, phenyl, xylyl, tolyl, benzyl, phenylethyl, chlorophenyl or dichlorophenyl;

the Y symbols are alike or different and each represent: either an $R^1$ radical or an $OR^2$ radical where $R^2$ is a hydrogen atom or a linear or branched $C_1$–$C_3$ alkyl radical.

The term "linear POSs (i)" is understood to mean POSs not exhibiting more than 3% of units other than the units of formulae (4), (5) and (6), for example units of formulae $R^1SiO_{3/2}$ (T) and/or $SiO_2$ (Q), the % symbols indicated express the number of T and/or Q units per 100 silicon atoms.

The inhibiting silicone compound preferably consists of a fluid of type (i), (2i), (3i) or (4i) having a viscosity of 25° C. which is at most equal to 1000 mPa.s, at least 60% by number of the $R^1$ symbols of which represent methyl radicals.

Examples of inhibiting silicone compounds which are highly suitable are:

as linear POSs (i): polydimethylsiloxanes which are blocked at each of the chain ends by a trimethylsiloxyl unit [in the formulae (4), (5) and (6): $R^1$=Y=CH$_3$] or by a hydroxyl group [in the formulae (4), (5) and (6): $R^1$=CH$_3$ and Y=OH] and which have a viscosity of 25° C. which is between 5 and 300 mPa.s;

as cyclic POSs (2i): cyclic polydimethylsiloxanes exhibiting from 3 to 9 units of formula (4) where $R^1$=CH$_3$;

and their various possible mixtures of type (3i) or (4i).

More specifically still, these POSs are, e.g.:

POS 1: linear α,ω-dihydroxylated polydimethylsiloxane oil with a viscosity of 25° C. equal to 50 mPa.s, of formula:

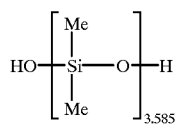

which has the following characteristics: calculated molecular mass=283.3 g; number of oxygen atoms per one mol of oil=4.59;

POS 2: cyclic polydimethylsiloxane oil comprising 4 dimethylsiloxyl units with a viscosity of 25° C. equal to 2 mPa.s which has the following characteristics: calculated molecular mass=296 g; number of oxygen atoms per one mol of oil=4;

POS 3: cyclic polydimethylsiloxane oil comprising 5 dimethylsiloxyl units with a viscosity of 25° C. equal to 2.5 mPa.s which has the following characteristics: calculated molecular mass =370 g; number of-oxygen atoms per one mol of oil =5.

In order to define in more detail the other silicon-based compounds which can be used as inhibitors, those will be added chosen from:

(i) a silane of formula:

$$(R^0)_e Si(OR^2)_{4-e} \qquad (7)$$

in which
the $R^0$ symbols are alike or different and each represent: a hydrogen atom; a linear or branched $C_1$–$C_8$ alkyl radical optionally substituted by one or more halogen(s); a $C_5$–$C_8$ cycloalkyl radical; or a $C_6$–$C_{12}$ aryl radical or an aralkyl radical having a $C_6$–$C_{12}$ aryl part and a $C_1$–$C_4$ alkyl part, the radical optionally being substituted on the aromatic part by one or more halogen(s), $C_1$–$C_3$ alkyl(s) and/or $C_1$–$C_3$ alkoxy(s);
the $R^2$ symbols are alike or different and each represent: a linear or branched $C_1$–$C_4$ alkyl radical or a $C_6$–$C_{12}$ aryl radical;
e is 0, 1, 2 or 3;

(2i) a silicone resin having a viscosity of 25° C. at most equal to 5000 mPa.s which exhibits the following distinguishing features:
it has in its structure units chosen from those of formulae $(R^3)_3SiO_{0.5}$ (M), $(R^3)_2SiO$ (D), $R^3SiO_{1.5}$ (T) and $SiO_2$ (Q), at least one of these units being a T unit or a Q unit, in which formulae the $R^3$ symbols, which are alike or different, mainly have the definitions given hereinabove with respect to the $R^0$ symbols;
the proportions of the T and/or Q units, expressed by the number of T and/or Q units per 100 silicon atoms, are greater than 10%;
it also has, per molecule, —$OR^4$ end groups carried by silicon atoms of the M, D and/or T units where
• the $R^4$ symbols, which are alike or different, each represent a hydrogen atom, a linear or branched $C_1$–$C_4$ alkyl radical or a $C_6$–$C_{12}$ aryl radical,
• the proportions of the —$OR^4$ ends, expressed by the mean number of these ends per 1 silicon atom, vary from 0.2 to 3.

In particular, these inhibiting silicones can be:
alkoxysilanes (i) of formula (4) in which:
the $R^0$ symbols, which are identical, each represent a linear or branched $C_1$–$C_4$ alkyl radical or a phenyl radical;
the $R^2$ symbols, which are identical, each represent a linear or branched $C_1$–$C_3$ alkyl radical;
e=1 or 2.

These alkoxysilanes (i) are, for example:

| $MeSi(OMe)_3$ | $C_6H_5Si(OMe)_3$ | $(C_6H_5)_2Si(OMe)_2$ |
|---|---|---|
| $MeSi(OC_2H_5)_3$ | $C_6H_5Si(OC_2H_5)_3$ | |
| | $(C_6H_5)_2Si(OC_2H_5)_2$ | | resins (2i): resins having a viscosity of 25° C. at most equal to 1000 mpa.s of MQ, MDQ, TD and MDT type, in the structures of which:

the R symbols of the M, D and T units are alike or different and each represent a linear $C_1$–$C_4$ alkyl radical;
the proportions of the T and/or Q units are greater than 30%;
there are —$OR^4$ end groups where the $R^4$ symbol represents a hydrogen atom or a linear $C_1$–$C_2$ alkyl radical and where the proportions of the said ends vary from 0.3 to 2.

These resins (2i) are, e.g.:
resins of TD type, in the structures of which:
the $R^3$ symbols of the D units are methyl radicals, whereas the $R^3$ symbols of the T units are n-propyl radicals;
the proportions of the T units, expressed by the number of T units per 100 silicon atoms, lie within the range from 40 to 65% and those of the D units, expressed by the number of D units per 100 silicon atoms, lie within the range from 60 to 35%;
the —$OR^4$ end groups, where the $R^4$ symbol represents an ethyl radical, are carried by silicon atoms of the D and T units and are present in proportions ranging from 0.3 to 0.5.

Quantitatively, it is preferable to incorporate the inhibitor in the distillation circuit in a proportion of at least 0.0001 weight %, preferably in a proportion of a percentage of between 0.0010 and 0.0100 weight % and more preferably still between 0.0020 and 0.0050 weight % with respect to the amount of AHHS present in the crude reaction mixture before distillation.

According to another advantageous characteristic of the invention, the bottoms $P_{III}$ from the column (III) are recycled by incorporating them in the feed flow for the column (I).

In the context of the preferred mode of the process according to the invention, the targeted AHHSs are dimethylmonohydrochlorosilane and/or methylmonohydrodichlorosilane and three distillation columns (I, II, III) are employed. For the isolation of $Me_2HSiCl$ in the context of this preferred mode, the following distillation parameters are chosen:

column (I):
pressures (in actual bars)
$0.1 \leq P_{tI} \leq 3$, preferably $1 \leq P_{tI} < 2$
$0.1 \leq P_{bI} \leq 3$, preferably $1 \leq P_{bI} \leq 2$
temperatures (° C.)
$60 \leq \theta_{tI} < 120$, preferably $80 \leq \theta_{tI} \leq 100$
$90 \leq \theta_{bI} < 150$, preferably $110 \leq \theta_{bI} \leq 130$
$r_I = 2 \pm 1$
$n_I = 5$ to 15
column (II):
pressures (in actual bars)
$1 \leq P_{tII} \leq 8$, preferably $4 \leq P_{tII} \leq 5$
$1 \leq P_{bII} \leq 8$, preferably $4 \leq P_{bII} \leq 5$
temperatures (° C.)
$35 \leq \theta_{tII} \leq 85$, preferably $60 \leq \theta_{tII} \leq 70$
$80 \leq \theta_{bII} \leq 140$, preferably $115 \leq \theta_{bII} \leq 125$
$r_{II} = 100 \pm 50$
$n_{II} = 10$ to 30
column (III):
pressures (in actual bars)
$10^{-4} \leq P_{tIII} \leq 1$, preferably
$10^{-3} \leq P_{tIII} \leq 100 \times 10^{-3}$
$10^{-4} \leq P_{bIII} \leq 1$, preferably
$10^{-3} \leq P_{bIII} \leq 100 \times 10^{-3}$ temperatures (° C.)

$35 \leq \theta_{tIII} \leq 57°$ C., preferably $35 \leq \theta_{tIII} \leq 38$ $63 \leq \theta_{bIII} \leq 87°$ C., preferably $63 \leq \theta_{bIII} \leq 66$ $r_{III} = 20 \pm 10$ $n_{III} = 30$ to 70.

This continuous distillation using a line of columns (I, II, III) relates to arrangements for adjusting the refluxes, flow rates, pressures, boilers and condensers which are conventional for persons skilled in the art.

As regards the injection of inhibitors into the circuit, preferably at the top of the column (I), the flow rates employed obviously depend on the dose of inhibitor which it is desired to fix in the condensed fluid emerging from the column (I) and feeding the second. By way of examples, for a flow rate at the outlet of the first column of the order of 1000 g/h, the flow rate for injection of the inhibitor is between 0.1 and 5 g/h, preferably between 0.4 and 1 g/h.

The process according to the invention thus makes it possible to obtain mono- or dialkylhydrochlorosilanes on an industrial scale with purities of greater than or equal to 90%, preferably of greater than or equal to 99%.

This is in fact a particularly attractive process for the industrial and economical production of mono- or dimethylhydrochlorosilanes.

According to another of these aspects, the present invention relates to a device for the implementation of the process as defined hereinabove. This device is characterized → in that it comprises at least three distillation columns (I, II, III), Δ the first being intended for the tailing of the redistribution catalyst and of its inhibitor, Δ the second being intended for the topping of the alkyldihydrohalosilanes;

Δ and the third for the separation between the targeted AHHS and the other products still present in the entering distillation flow, → and in that these columns are equipped with means for incorporation of at least one inhibitor which is active with respect to products capable of catalysing side reactions in which the targeted AHHS is converted into other undesirable byproducts, these means for incorporation preferably being means for conveying inhibitors, advantageously, into the condensate produced at the top of column (I).

The invention will be better understood in the light of the examples which follow and which describe a preferred embodiment of the device according to the invention and a preferred embodiment of the process.

The more detailed description of the device according to the invention is made with reference to the single appended drawing, which represents a block diagram of the preferred embodiment of the device according to the invention.

As shown in the FIGURE, the device comprises a reactor 1 and an intermediate container 2 inserted between the reactor 1 and a line of three distillation columns (I, II, III).

The reactor 1 acts as the site of the redistribution stage (a). The inhibitor of the redistribution catalyst, such as $AlCl_3$, is introduced into the reactor 1 at the end of the reaction. This reactor 1 is connected to the intermediate container 2 via a pipe 3 which makes it possible to decant the contents of the first into the second. The crude redistribution reaction mixture thus decanted can comprise some light volatile compounds, such as, for example, $Me_2H_2Si$. These volatiles, produced in the container 2, can be recovered in the gaseous form or in the liquid form after condensation, in order to be enhanced in value or destroyed by combustion. This corresponds to the outlet A in the drawing.

The reaction mixture present in the intermediate container 2 can be subsequently conveyed to the distillation column (I) via a pipe 4, optionally using a pump 21. The latter is connected to the column (I) at the feed point corresponding to the conventional distillation calculation (stages of concentrations and stages of stripping).

This column (I), as well as its homologues (II) and (III), is of the type of those known to persons skilled in the art. They can be columns with bubble trays, perforated trays, valve trays or any type of stacked packing.

As regards the columns (I, II, III) of the device represented in the appended drawing, it should be observed that each of them exhibits a bottom and a top between which is established a temperature gradient. Each head of a column (I, II, III) is associated with condensation means ($5_I$, $5_{II}$, $5_{III}$) for producing liquid or gaseous distillates $D_I$, $D_{II}$, $D_{III}$. Each bottom of a column (I, II, III) is equipped with boilers ($6_I$, $6_{II}$, $6_{III}$) suitable for providing the heat energy needed for the change from liquid state→vapour state within the column.

The condensers ($5^I$, $5_{II}$, $5_{III}$) and the boilers ($6_I$, $6_{II}$, $6_{III}$) are connected to the corresponding columns via respectively pipes ($7_I$, $7_{II}$, $7_{III}$) on the one hand, and ($8_I$, $8_{II}$, $8_{III}$), on the other hand.

The condenser $5_I$ makes possible the conversion of the vapours of light compounds from the column (I) into a liquid condensate, collected in a tank 9.

The column (I) is also provided with means 11, 12, 13 for the incorporation of at least one inhibitor, advantageously the cyclic polysiloxane $D_5$. These means comprise a vessel 11 for the inhibitor connected, via a pipe 12, to the tank 9 for collecting the liquid condensates obtained from the topping distillation fraction from the column (I). This pipe 12 is equipped with a flowmeter 13 which makes it possible to quantitatively determine the small amounts of inhibitor injected.

The inhibitor/liquid topping condensate mixture, which comprises compounds such as $MeH_2SiCl$, $Me_2H_2Si$, $Me_2HSiCl$, $MeH_3Si$, $Me_4Si$, $Me_3SiCl$ and $Me_2SiCl_2$, is conveyed in a pipe 15 using a pump 14 to a bypass comprising a branch 16, forming a pipe for the reflux $R_I$, and a branch 17 for feeding the column (II) with fluid or distillate $D_I$.

The pipe 16 for the reflux emerges in the top of the column (I), whereas the pipe 17 emerges at the feed point of the column (II), which feed point is chosen in the same way as that of the column (I). This pipe 17 is equipped with a valve 18 which makes it possible to adjust the flows $R_I$ and $D_I$.

For example, a third of the flow originating from the pipe 15 is conveyed via the pipe 17 and the remaining two thirds via the reflux pipe 16.

The bottoms $P_I$ from the column (I) are discharged out of the distillation circuit via a pipe 19. The products collected at this outlet $P_I$ are, for example, the redistribution catalyst (e.g. $AlCl_3$), the inhibitor, which can be a cyclic polysiloxane (such as decamethylpentasiloxane=$D_5$), and the heaviest organochlorosilanes, such as, for example, $Me_2SiCl_2$.

The vapours condensed into liquid which are collected at the outlet of the condenser $5_{II}$ associated with the top of the column (II) flow back via a pipe 20 to the top of this column (II).

The light organosilane gases which are not converted into liquid by the condenser $5_{II}$ constitute the distillate $D_{II}$ and are discharged via a pipe 22 for the purposes of being enhanced in value or of being destroyed by combustion.

The topping of the light products generated by the column (II) correspondingly results in the production of liquid bottoms $P_{II}$ intended to feed the column (III). $P_{II}$ comprises, for example, $Me_2H_2SiCl$, $MeHSiCl_2$, $Me_2SiCl_2$ and $Me_3SiCl$.

$P_{II}$ is conveyed to the column (III) via a pipe 23 (with or without a pump, preferably without a pump) at a feed point chosen by employing the same methods as those used for the feed points for the columns (I) and (II).

The top of the column (III) is equipped with a pipe 24 for collecting the liquid condensate comprising the AHHS which it is desired to purify. The condenser $5_{III}$ is also connected to a pipe 25 for discharge of the vented products. The top of the column (III) is furthermore equipped with a pipe 26 for the reflux $RI$, formed of pure or substantially pure AHHS.

The bottom of the column (III) is, for its part, provided with a pipe 28 for collecting the liquid $P_{III}$ which makes it possible to convey the latter to a point for enhancing in value, recovering or destroying the recovered compounds, which, for example, can be $Me_3SiCl$ and $Me_2SiCl_2$.

According to an alternative embodiment of this device, inter alia, the means for injection 11, 12, 13 of the inhibitor could be connected, in addition to or instead of connecting them to the return loop or loop for the reflux $R_I$ of the top of the column (I), to the pipe 17 for feeding the column (II) situated downstream of this loop for the reflux $R_I$.

It is also possible, according to other alternative forms, to introduce the inhibitor at the top of columns (II) and/or (III).

The use of the process according to the invention and in particular of the distillation stage (c), which involves the line of 3 distillation columns (I to III), is illustrated by the various tests reported hereinbelow.

EXAMPLE

1)—Products Employed

The synthesis under consideration in the present examples is that of $Me_2HSiCl$ (=targeted AHHS) prepared by redistributing $MeHSiCl_2$ and $Me_3SiCl$ in a stage (a) in the presence of Lewis acid catalyst, in this case $AlCl_3$. This reaction takes place in the reactor 1.

The inhibitor employed is a cyclic polydimethylsiloxane (PDMS) oil comprising 5 dimethylsiloxyl units ($D_5$), with a viscosity of 25° C.=2.5 mPa.s, which has the following characteristics:

Calculated molecular mass=370 g; number of oxygen atoms per one molecule of oil=5.

2)—Equipment Used

The device as described hereinabove is used. The continuous distillation columns (I to III) employed comprise a Sulzer-Mellapack stacked packing, the height of which corresponds to the desired number of theoretical plates. The other equipment, condensers, boilers, valves, and the like, is of known types.

3)—Procedure for the Stage (a)

5490 g of $Me_3SiCl$ and 2900 g of $MeHSiCl_2$ are charged with stirring to the stainless steel reactor 1, purged beforehand with nitrogen, in order to obtain an $MeH/Me_3$ molar ratio of 0.5.

The catalyst, i.e. 252 g of anhydrous aluminium chloride, is added to this mixture.

The reactor is closed and the pressure is adjusted to $10 \times 10^5$ Pa with nitrogen and then to atmospheric pressure. Stirring is provided by a 4-bladed turbine. The stirring rate is set at 100 revolutions/min. The reactor is heated to 100° C. and the pressure becomes established at $4.5 \times 10^5$ Pa. The temperature is maintained at 100° C. for 2 hours. 294 g of the POS inhibiting compound are introduced into the reactor over a few minutes. The combined mixture is maintained at 100° C. for ½ h with stirring and then the reactor is cooled to 20° C. The residual pressure of $1.5 \times 10^5$ Pa is removed by degassing. 8757 g of reaction mixture comprising 1313 g of $Me_2HSiCl$ and the inactive catalyst are thus obtained.

4)—Stage (c): Distillation

The crude reaction mixture comprising $D_5$ is withdrawn from the vessel 2 in order to feed the column (I) according to a flow rate of 1000 g/h.

For continuous operation, the reactor 1 is fed with $Me_3SiCl$, $MeHSiCl_2$, $AlCl_3$ and cyclic PDMS $D_5$ so that it is possible to produce the crude reaction mixture with $D_5$ added at the rate of at least 1000 g/h. This mixture, thus produced, is transferred batchwise into the vessel 2.

The material balance (produced by gas chromatography) at the inlet of the column (I) is as follows:

150 g/h of $Me_2HSiCl$ (targeted AHHS)
380 g/h of $Me_2SiCl_2$
380 g/h of $Me_3SiCl$
20 g/h of $MeHSiCl_2$
41 g/h of heavy products=$D_5$+$AlCl_3$
29 g/h of light products=$Me_2H_2Si$, $MeH_2SiCl$, $Me_4Si$ and other light products.
1000 g/h The distillation parameters for the column (I) are given hereinbelow:

temperatures (° C.)
$\theta_{tI}=87.5$, $\theta_{bI}=116$ pressures (in actual bars)
$P_{tI}=1.5$, $P_{bI}=1.55$ $n_I=10$ (feed point at the 8th theoretical stage from the bottom)

$$r_I = \frac{R_I}{D_I} = 1.8$$

=1.8

The heat energy produced by the boiler $6_I$ is: 207 kcal/h.

0.7 g/h of $D_5$ is introduced continuously into the vessel 9. These 0.7 g/h are distributed in a proportion of 0.45 g/h in $R_I$ and 0.25 g/h in $D_I$.

Analyses of $P_I$ by gas chromatography makes it possible to calculate the following flow rates at the bottom of column (I):

| | |
|---|---|
| $AlCl_3$ + $D_5$ | 41 g/h |
| $Me_2SiCl_2$ | 41 g/h |
| DI, which comprises: | |
| $Me_2HSiCl$ | 150 g/h |
| $Me_2SiCl_2$ | 339 g/h |
| $Me_3SiCl$ | 380 g/h |
| $MeHSiCl_2$ | 20 g/h |
| Light products | 29 g/h |
| $D_5$ | 0.25 g/h |
| | 918.25 g/h | is introduced into the column (II) via the pipe 17.

The distillation parameters for this column (II) are given hereinbelow:

temperatures (° C.)
$\theta_{tII}=63$, $\theta_{bII}=118$ pressures (in actual bars)
$P_{tII}=4.4$, $P_{bII}=4.42$ $n_{II}=20$ (feed point at the 8th theoretical stage from the bottom)

$$r_{II} = \frac{R_{II}}{D_{II}} = \text{approximately } 70$$

=approximately 70

The heat energy produced by boiler $6_{II}$ is: 102 kcal/h.

Analyses of $D_{II}$ and $P_{II}$ by gas chromatography give respectively the following results:

$D_{II}$=29 g/h, comprising essentially $MeH_2SiCl$, $Me_2H_2Si$ and other light products,

| $P_{II}$ = | $Me_2HSiCl$ | 150 g/h |
| | $Me_2SiCl_2$ | 339 g/h |
| | $Me_3SiCl$ | 380 g/h |
| | $MeHSiCl_2$ | 20 g/h |
| | D5 | 0.25 g/h |
| | | 889.25 g/h |

$D_{II}$ is discharged via the vent 22 and $P_{II}$ is introduced into the column (III) via the pipe 23.

The distillation parameters for this column (III) are given hereinbelow:

temperatures (° C.)
 $\theta_{tIII}$=36, $\theta_{bIII}$=63.5 pressures (in actual bars)
 $P_{tIII}$=30×10$^{-3}$, $P_{bIII}$=35×10$^{-3}$ $n_{III}$=48 (feed point at the 27th theoretical stage from the bottom)

$r_{III}$=

$$r_{III} = \frac{R_{III}}{D_{III}} = \text{approximately } 20$$

=approximately 20

The heat energy produced by the boiler $6_{III}$ is: 180 kcal/h.

Analyses of $D_{III}$ and $P_{III}$ by gas chromatography give respectively the following results:

$D_{III}$=150 g/h of $Me_2HSiCl$ with a purity of 99% comprising mainly $MeHSiCl_2$ as impurity.

| $P_{III}$ = | | |
| --- | --- | --- |
| $Me_3SiCl$ | | 380 g/h |
| $Me_2SiCl_2$ | | 339 g/h |
| $MeHSiCl_2$ | | 20 g/h |
| $D_5$ | | 0.25 g/h |
| | | 739.25 g/h |

The vent 25 gives off no or virtually no $Me_2H_2$

5) Comparative:

Distillation (c) without injection of $D_5$ at the top of column (I).

$D_{III}$=$Me_2HSiCl$ (75 g/h) comprising more than 1% of $Me_2H_2Si$.

The vents 22 and 25 allow large amounts of $Me_2H_2$ produced by the interfering dismutation of $Me_2HSiCl$ to escape.

Without injection of $D_5$, only 50% of the $Me_2HSiCl$ feeding the distillation is recovered, whereas, with the injection of $D_5$, 100% of it is recovered.

What is claimed is:

1. A process for the preparation of alkylmonohydrohalosilanes which are liable to be subject to a dismutation catalysed by at least one Lewis acid, this process comprising the following steps:
   (a) redistribution of a reaction mixture between at least one first compound of formula (1): $(R)_a(H)_bSiX_{4-a-b}$, and at least one second compound of formula (2): $(R')_cSiX_{4-c}$, (1) and (2) wherein:
   a=0, 1,2 or 3; b=1,2 or 3; c=1, 2, 3 or 4 and a+b≦3;
   R and R' are identical to or different from one another and are alkyl or aryl radicals;
   the X substituents are identical to or different from one another and correspond to a halogen;
   with the further proviso that at least one X atom is present in at least one of the two compounds of formulae (1) and (2), said redistribution taking place in the presence of a Lewis acids catalyst;
   (b) addition into the reaction mixture of at least one inhibitor of the redistribution catalyst; and
   (c) separation and collection of the alkylmonohydrohalosilanes formed in the crude redistribution reaction mixture (a);
   the crude reaction mixture being subjected to a distillation treatment involving at least one distillation column, and
   at least in a portion of the distillation circuit, the formed alkylmonohydrohalosilanes are in the presence of at least one inhibitor of any product capable of behaving as a redistribution catalyst with respect to said alkylmonohydrohalosilanes.

2. A process according to claim 1, wherein in step a),
   R and R' are methyl, ethyl, propyl or phenyl
   the X substituents are Cl, and
   the catalyst is $AlCl_3$, $ZrCl_4$, $KAlCl_4$, $CuCl$, $H_3BO_3$ or $BF_3$.

3. A process according to claim 1, wherein the distillation stage (c) comprises:
   ($c_1$) employing a line of at least two distillation columns, column (I) and column (II);
   ($c_2$) ensuring that the fluid comprising the alkylmonohydrohalosilanes is brought into contact with the inhibitor:
   (i) by injecting a fluid comprising the inhibitor, on the one hand, at least into in column (I) of the distillation line, countercurrentwise with respect to the fluid vapour comprising the alkylmonohydrohalosilanes,
   and, on the other hand, into the feed fluid for column (II), or
   (ii) by mixing the inhibitor with the feed fluid for at least one of the columns of the line.

4. A process according to claim 3, wherein the mixing (ii) occurs in column (II).

5. A process according to claim 3, wherein, in the stage ($C_2$), it is ensured that the fluid comprising the formed Alkylmonohydrohalosilanes is brought into contact with the inhibitor by mixing the latter with a condensate ($D_I$) produced and collected at the top of column (I) and by providing for the reflux $R_I$ of at least a portion of this condensate into this column (I); and
   the reflux ratio $r_I$=$R_I/D_I$, with $R_I$=reflux at the top of column (I) and
   $D_I$=distillate at the top of column (I), being adjusted to between 0.5 and 3.

6. A process according to claim 3, wherein
   in stage ($c_I$), the distillation line comprises three distillation columns, respectively:
   a column (I) for tailing the heavy compounds of the crude reaction mixture, a column (II) for topping the light compounds of the crude reaction mixture, and a column (III) for final separation of the alkylmonohydrohalosilanes; and the column (I) is fed with the crude reaction mixture while having taken care to set the pressure parameters ($P_{bI}$, $P_{tI}$) and temperature parameters ($\theta_{bI}$, $\theta_{tI}$) for the bottom and top of the column, number $n_I$ of plates and reflux ratio $r_I$ so that a distillation fraction comprising the formed alkylmonohydrohalosilanes is recovered at the top of column (I), this fraction is condensed into a liquid which is fractionated into a reflux $R_I$ and into a distillate $D_I$;

the column (II) is fed with $D_I$ while having taken care to set the pressure parameters ($P_{bII}$, $P_{tII}$) and temperature parameters ($\theta_{bII}$, $\theta_{tII}$) for the bottom and top of the column, number $n_{II}$ of plates and reflux ratio $r_{II}$ so as to produce and collect:

on the one hand, at the top of column (II), a distillation fraction forming the distillate ($D_{II}$) and comprising alkylhydrohalosilanes and alkylsilanes with boiling points which are below that of the targeted alkylmonohydrohalosilanes, and on the other hand, at the bottom of column (II), a distillation fraction $P_{II}$ comprising the formed alkylmonohydrohalosilanes; and the column (III) is fed with $P_{II}$ while having taken care to set the pressure parameters ($P_{bIII}$, $P_{tIII}$) and temperature parameters ($\theta_{bIII}$, $\theta_{tIII}$) for the bottom and top of the column, number $n_{III}$ of plates and reflux ratio $r_{III}$ so as to produce and collect:

on the one hand, at the top of the column, a distillate $D_{III}$ composed essentially of the formed alkylmonohydrohalosilanes, on the other hand, at the bottom of the column, a distillation fraction forming the bottoms $P_{III}$ comprising alkylhydrohalosilanes and alkylhalosilanes with boiling points which are greater than or equal to that of the formed alkylmonohydrohalosilanes.

7. A process according to claim 1, wherein the inhibitor is:

a cyclic polyorganosiloxane comprising from 4 to 10 Si atoms;

a hydroxylated or non-hydroxylated, linear or branched polyorganosiloxane having from 2 to 100 silicon atoms;

an optionally alkoxylated polyorganosiloxane resin;

an optionally alkoxylated silane;

a monofunctional or polyfunctional alcohol; or a ketone.

8. A process according to claim 7, wherein the inhibitor is:

octamethyltetrasiloxane, decamethylpentasiloxane, or a polydimethylsiloxanes with a viscosity of 50 mPa.s.

9. A process according to claim 1, wherein the inhibitor is incorporated in a proportion of at least 0.0001 weight % with respect to the amount of alkylmonohydrohalosilanes present in the crude reaction mixture before distillation.

10. A process according to claim 9, wherein the inhibitor is incorporated in a proportion of between 0.0020 and 0.0050 weight %.

11. A process according to claim 6, wherein the formed alkylmonohydrohalosilanes is dimethylmonohydrochlorosilane, and wherein the following distillation parameters are chosen:

column (I):
pressures (in actual bars)
$0.1 \leq P_{tI} \leq 3$, preferably $1 \leq P_{tI} \leq 2$
$0.1 \leq P_{bI} \leq 3$, preferably $1 \leq P_{bI} \leq 2$
temperatures (° C.)
$60 \leq \theta_{tI} \leq 120$, preferably $80 \leq \theta_{tI} \leq 100$
$90 \leq \theta_{bI} \leq 150$, preferably $110 \leq \theta_{bI} \leq 130$
$r_I \geq 1$
$n_I = 5$ to 15 column (II):
pressures (in actual bars)
$1 \leq P_{tII} \leq 8$, preferably $4 \leq P_{tII} \leq 5$
$1 \leq P_{bII} \leq 8$, preferably $4 \leq P_{bII} \leq 5$
temperatures (° C.)
$30 \leq \theta_{tII} \leq 85$, preferably $60 \leq \theta_{tII} \leq 70$
$80 \leq \theta_{bII} \leq 140$, preferably $115 \leq \theta_{bII} \leq 125$
$r_{II} = 100 \pm 50$
$n_{II} = 10$ to 30 column (III):
pressures (in actual bars)
$10^{-4} \leq P_{tIII} \leq 1$, preferably
$10^{-3} \leq P_{tIII} \leq 100 \times 10^{-3}$
$10^{-4} \leq P_{bIII} \leq 1$, preferably
$10^{-3} \leq P_{bIII} \leq 100 \times 10^{-3}$
temperatures (° C.)
$35 \leq \theta_{tIII} \leq 57°$ C., preferably $35 \leq \theta_{tIII} \leq 38$
$63 \leq \theta_{bIII} \leq 87°$ C., preferably $63 \leq \theta_{bIII} \leq 66$
$r_{III} = 20 \pm 10$
$n_{III} = 30$ to 70.

* * * * *